US00PP17113P2

(12) United States Plant Patent
Jonkers

(10) Patent No.: US PP17,113 P2
(45) Date of Patent: Sep. 26, 2006

(54) ***IMPATIENS* PLANT NAMED 'BUTLY SALEY'**

(50) Latin Name: ***Impatiens walleriana*×*Impatiens pseudoviola***
Varietal Denomination: Butly Saley

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 9 days.

(21) Appl. No.: 11/209,972

(22) Filed: Aug. 23, 2005

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
(74) *Attorney, Agent, or Firm*—Jondle & Associates P.C.

(57) ABSTRACT

An *Impatiens* cultivar particularly distinguished by large light salmon-colored flowers with bright blotches, large leaves, good vigor, and a branching and trailing habit is disclosed.

1 Drawing Sheet

Genus and species: *Impatiens walleriana*×*Impatiens pseudoviola.*
Variety denomination: 'Butly Saley'.

BACKGROUND OF THE NEW PLANT

The present invention comprises a new and distinct cultivar of *impatiens,* botanically known as *Impatiens walleriana*×*Impatiens pseudoviola*, and hereinafter referred to by the cultivar name 'Butly Saley'. The new cultivar originated from a hybridization made in the year 2003 in Andijk, The Netherlands. The female parent was 'IMY-122-2', an unpatented proprietary *impatiens* line having salmon-colored flowers with eyes, while the male parent was 'SPZ-1-21', a lavender-flowered unpatented proprietary *impatiens* line.

The new cultivar was created in 2003 in Andijk, The Netherlands and has been asexually reproduced repeatedly by vegetative cuttings and tissue culture in Gilroy, Calif. and Andijk, The Netherlands over a one and a half year period. The plant has also been trialed at Gilroy, Calif., Litchfield, Mich. and Andijk, The Netherlands. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif. and Andijk, The Netherlands.

1. Large light salmon-colored flowers with bright blotches;
2. Large leaves;
3. Good vigor; and
4. A branching and trailing habit.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is of three four and a half month-old plants grown in an 8-inch pot in Andijk, The Netherlands in a greenhouse in a late winter/spring trial setting.

The accompanying photograph shows overall plant habit including blooms, buds and foliage; the inset shows mature inforescences.

DESCRIPTION OF THE NEW CULTIVAR

The following detailed descriptions set forth the distinctive characteristics of 'Butly Saley'. The data which defines these characteristics were collected from asexual reproductions carried out in Gilroy, Calif. The plant history was taken on 12-week-old plants grown in 6-inch pots in a poly-covered greenhouse in the spring/early summer season. Color readings were taken under natural light in the greenhouse. Color references are primarily to The R.H.S. Colour Chart of The Royal Horticultural Society of London (R.H.S.) (2001). Texture description details were observed under a dissecting microscope.

DETAILED BOTANICAL DESCRIPTION

Classification:
- *Botanical.*—*Impatiens walleriana*×*Impatiens pseudoviola.*
- *Common name.*—*Impatiens.*

Parentage:
- *Female parent.*—'IMY-122-2' proprietary line (unpatented).
- *Male parent.*—'SPZ-1-21' proprietary line (unpatented).

Growth:
- *Form.*—Slightly upright and semi-trailing.
- *Growth and branching habit.*—Grow branching; vigorous; pinching of the terminal apices enhances branching and floriferousness.
- *Height (from soil level to top of blooms).*—18–22 cm.
- *Width (including flowers).*—20–30 cm.
- *Time to produce a finished flowering plant.*—8–10 weeks for a 4-inch pot.

*Outdoor plant performance.*—In shade, has intermediate flowering but is free-flowering all year; has some heat tolerance; use in hanging baskets, mixed containers, window boxes, and mass plantings.

*Time to initiate and develop roots.*—10–21 days.

*Root description.*—Fibrous, fleshy, and white.

Leaves:

*Arrangement.*—*Alternate, whorls.*

*Length.*—3.2–4.5 cm.

*Width.*—2.4–3.0 cm.

*Shape.*—Ovate.

*Margin.*—Crenate with one ciliate at each lobe.

*Apex.*—Broadly acute.

*Base.*—Attenuate.

*Color.*—Upper surface: Closest to RHS 147A. Lower surface: RHS 147B.

*Texture.*—Glabrous.

*Venation.*—Pinnate.

*Venation color.*—RHS 144B.

*Petiole.*—Length: 0.8–1.4 cm. Diameter: 0.1 cm. Color: RHS 144B. Texture: Glabrous.

Stems:

*Length.*—15.0–20.0 cm.

*Diameter.*—0.3–0.4 cm.

*Internode length.*—2.0–3.0 cm.

*Color.*—RHS 144A.

*Texture.*—Glabrous.

*Stem anthocyanin.*—Present in small irregular blotches, reddish brown.

*Pedicel.*—Length: 1.3–1.5 cm. Diameter: 0.1 cm. Color: RHS 144B. Texture: Glabrous.

*Peduncle.*—Length: 2.2–2.4 cm. Diameter: 0.1 cm. Color: RHS 144B. Texture: Glabrous.

Flower buds:

*Shape.*—Ovate.

*Diameter.*—0.5–0.7 cm.

*Length.*—0.7–1.2 cm.

*Color at tight bud.*—RHS 69C.

Inflorescence:

*Blooming habit.*—Continuous and freely all through the spring, summer and fall.

*Inflorescences type.*—Racemes in leaf axis and in leaf whorls.

*Number of flowers per raceme and/or whorl.*—Approximately 10–15, including buds.

*Number of flowers per plant.*—Approximately 75–100.

*Lastingness of individual blooms on the plant.*—4–8 days.

*Fragrance.*—None.

Flowers:

*Floret form.*—5 petals, 1 standard or dorsal (free); 2 lateral or lobed pairs (wing petals), deeply lobed.

*Floret diameter.*—2.5–3.0 cm.

*Floret height.*—2.4–2.6 cm.

*Color, immature flowers, upper surface.*—Dorsal petal: Between RHS 49B and RHS 49C. Lateral petal: Between RHS 49B and RHS 49C with blotches on the basal one-third of the petal between RHS 50A and RHS 50B.

*Color, immature flowers, lower surface.*—Dorsal petal: RHS 49D, but lighter. Lateral petal: RHS 49D, but lighter.

*Color, mature flowers, upper surface.*—Dorsal petal: Between RHS 49C and RHS 49D. Lateral petal: Between RHS 49C and RHS 49D with blotches on the basal one-third of the petal between RHS 50A and RHS 50B.

*Color, mature flowers, lower surface.*—Dorsal petal: RHS 49D, but lighter. Lateral petal: RHS 49D, but lighter.

Petals:

*Quantity.*—5 .

*Dorsal.*—Length: 1.2–1.3 cm. Width: 1.4–1.7 cm. Shape: Obovate. Apex: Emarginate. Base: Fused. Margin: Entire. Texture: Papillose.

*Lateral.*—Length: 1.3–1.4 cm. Width: 0.6–1.1 cm. Shape: Spathulate. Apex: Emarginate. Base: Fused. Margin: Entire. Texture: Papillose.

Sepals:

*Quantity.*—3, 1 larger than the others, with a spur.

*Large sepal.*—Color: RHS 157D, but lighter; RHS 144B keel. Length: 1.0–1.2 cm. Width: 0.5–0.7 cm. Shape: Broadly elliptical. Apex: Emarginate. Base: Fused. Margin: Entire. Texture: Glabrous. Spur: Color: RHS 145C with a pink, RHS 49D, overlay hue and a 1.0 mm tip of RHS 165A. Length: 2.4–2.5 cm.

*Small sepal.*—Color: RHS 144B. Length: 0.3–0.4 cm. Width: 0.075 cm. Shape: Linear. Apex: Acute. Base: Fused. Margin: Entire. Texture: Glabrous.

Reproductive organs:

*Stamens.*—5; more or less fused by the anthers and covering the ovary.

*Pollen cap color.*—Slight hue of RHS 69A.

*Pollen amount.*—Not observed.

*Pistil.*—1, complete.

Fruit and seed set: Has not been observed.

Disease and insect resistance: Has not been observed

COMPARISON WITH KNOWN CULTIVARS

'Butly Saley' differs from the female parent, 'IMY-122-2' proprietary line (unpatented), in that 'Butly Saley' has a lighter flower color with brighter blotches, larger flowers, a branched habit with more vigor, and a more trailing habit than 'IMY-122-2'. 'Butly Saley' differs from the male parent, 'SPZ-1-21' proprietary line (unpatented), in that 'Butly Saley' has salmon-colored flowers, larger flowers, has more vigor, and is more floriferous than 'SPZ-1-21'.

'Butly Saley' differs from the commercial cultivar 'Fify Salmon' (U.S. Plant Pat. No. 11,559) in that 'Butly Saley' has larger, lighter salmon-colored flowers with bright blotches, larger leaves, and a more vigorous plant habit than 'Fify Salmon'.

I claim:

1. A new and distinct cultivar of *Impatiens* plant as shown and described herein.

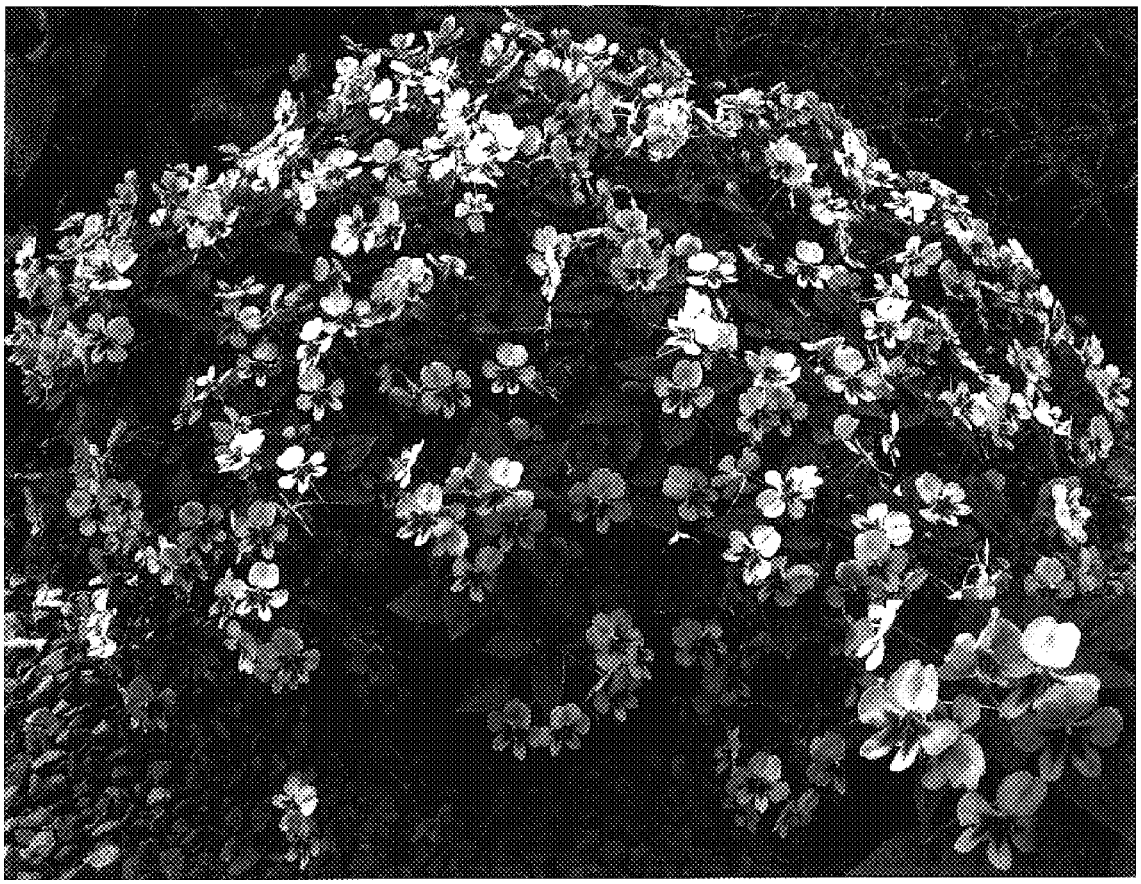

* * * * *